US010336856B2

(12) United States Patent
Stache et al.

(10) Patent No.: US 10,336,856 B2
(45) Date of Patent: Jul. 2, 2019

(54) ALKOXYSILANE- AND ALLOPHANATE-FUNCTIONALIZED COATING MATERIALS

(71) Applicant: Evonik Degussa GmbH, Essen (DE)

(72) Inventors: Wiebke Stache, Herten (DE); Tobias Unkelhäußer, Dülmen (DE); Annegret Lilienthal, Dorsten (DE); Sina Ballauf, Duisburg (DE); Sabine Naumann, Herne (DE); Bartholomäus Buchczik, Marl (DE)

(73) Assignee: Evonik Degussa GmbH, Essen (DE)

( * ) Notice: Subject to any disclaimer, the term of this patent is extended or adjusted under 35 U.S.C. 154(b) by 95 days.

(21) Appl. No.: 15/614,763

(22) Filed: Jun. 6, 2017

(65) Prior Publication Data
US 2017/0369631 A1 Dec. 28, 2017

(30) Foreign Application Priority Data

Jun. 27, 2016 (EP) ..................... 16176312

(51) Int. Cl.
C08G 18/00 (2006.01)
C08G 18/71 (2006.01)
C08G 18/38 (2006.01)
C08G 18/77 (2006.01)
C08G 18/78 (2006.01)
C09D 175/04 (2006.01)
C07F 7/18 (2006.01)
C08G 18/73 (2006.01)
C08G 18/75 (2006.01)
C08G 18/80 (2006.01)
C08G 18/24 (2006.01)
C09D 175/12 (2006.01)
C08G 18/32 (2006.01)

(52) U.S. Cl.
CPC .......... C08G 18/718 (2013.01); C07F 7/1804 (2013.01); C07F 7/1892 (2013.01); C08G 18/244 (2013.01); C08G 18/3206 (2013.01); C08G 18/3893 (2013.01); C08G 18/73 (2013.01); C08G 18/755 (2013.01); C08G 18/778 (2013.01); C08G 18/7837 (2013.01); C08G 18/809 (2013.01); C09D 175/04 (2013.01); C09D 175/12 (2013.01); C08G 18/3203 (2013.01)

(58) Field of Classification Search
CPC .............. C08G 18/7837; C08G 18/289; C08G 18/718; C08G 18/3893
See application file for complete search history.

(56) References Cited

U.S. PATENT DOCUMENTS 4,772,672 A 9/1988 Isozaki
5,516,559 A 5/1996 Roeckrath et al.
7,812,087 B2* 10/2010 Ludewig ................ C08G 18/10
  524/589
8,013,099 B2 9/2011 Poppe et al.
8,067,522 B2* 11/2011 Ludewig ............ C08G 18/4825
  525/474
8,163,390 B2 4/2012 Gruber et al.
9,163,390 B2* 10/2015 Pacaci ...................... E04B 1/24
9,175,126 B2 11/2015 Albrecht et al.
9,266,825 B2 2/2016 Lomoelder et al.
10,093,765 B2* 10/2018 Stache .................. C07F 7/1872
10,093,826 B2* 10/2018 Stache ................. C09D 175/04
2009/0018302 A1* 1/2009 Laas .................... C08G 18/289
  528/17
2009/0326146 A1 12/2009 Sepeur et al.
2010/0010113 A1 1/2010 Schwalm et al.
2010/0092686 A1 4/2010 Laryea et al.
2011/0082254 A1 4/2011 Sepeur et al.
2011/0082273 A1 4/2011 Laas et al.
2012/0029143 A1 2/2012 Sepeur et al.
2015/0191625 A1* 7/2015 Lomoelder .......... C08G 18/718
  524/91
2015/0232609 A1 8/2015 Spyrou et al.
2015/0329751 A1 11/2015 Stache et al.
2015/0329752 A1 11/2015 Albrecht et al.
2016/0297974 A1 10/2016 Stache et al.
2017/0269627 A1* 9/2017 Cook ...................... G05F 3/267

FOREIGN PATENT DOCUMENTS

CA 1081389 7/1980
DE 2356768 B1 1/1975
(Continued)

OTHER PUBLICATIONS

Kozakiewicz et al., "New Family of Functionalized Crosslinkers for Heat-Curable Polyurethane Systems—A Preliminary Study," copyright 2011, Progress in Organic Coatings, vol. 72, pp. 120-130 (11 pages).
Stache et al., U.S. Appl. No. 15/619,897, filed Jun. 12, 2017.

Primary Examiner — Rip A Lee
(74) Attorney, Agent, or Firm — Philip P. McCann; Nexsen Pruet, PLLC

(57) ABSTRACT

An alkoxysilane-functionalized and allophanate-functionalized coating material including a) a binder component of 10-99 wt % of at least one reaction product of I. and II. wherein I includes A) at least one alkoxysilane-containing monourethane A) of the formula 1 $R_n(OR^1)_{3-n}Si-R^2-NH-(C=O)-OR^3$ wherein R, $R^1$, $R^2$ and $R^3$ represent hydrocarbon radicals having 1-8 carbon atoms, and n represents 0-2, and B) at least one diisocyanate B), and II includes the subsequent reaction of C) with at least one diol and/or polyol C), in a ratio of NCO groups of reaction product I to OH groups of the diol and/or polyol II. C) of 1.0:1.5 to 1.0:0.6; b) 1-90 wt % of at least one further binder component distinct from a) a hydroxyl-containing or amino-containing binder component, c) 0-50 wt % of at least one polyisocyanate having an NCO functionality of at least 2, d) 0-5 wt % of at least one catalyst, wherein components a)-d) add up to 100 wt %.

25 Claims, No Drawings

(56) References Cited

FOREIGN PATENT DOCUMENTS

| | | |
|---|---|---|
| DE | 102005041953 A1 | 3/2007 |
| DE | 102005041954 A1 | 3/2007 |
| DE | 102005045228 A1 | 4/2007 |
| DE | 102009047964 A1 | 4/2011 |
| EP | 1204701 B1 | 9/2005 |
| EP | 2676982 A1 | 12/2013 |
| WO | 9211328 A1 | 7/1992 |
| WO | 9315849 A1 | 8/1993 |
| WO | 2008043722 A1 | 4/2008 |
| WO | 2008131715 A1 | 11/2008 |

\* cited by examiner

ALKOXYSILANE- AND ALLOPHANATE-FUNCTIONALIZED COATING MATERIALS

This application claims the benefit of European Application No. 16176312.3 filed on Jun. 27, 2016, the disclosure of which is expressly incorporated herein by reference.

BACKGROUND

The present invention relates to alkoxysilane- and allophanate-functionalized coating materials, to a process for the production thereof and to the use thereof.

Polyurethanes have been established for many decades as high-value components for paint, adhesive, sealant and plastics systems. It is possible here for additional alkoxysilane groups to play an important role, for example with regard to network density, chemicals resistance and scratch resistance, primarily through the formation of siloxane and polysiloxane structures.

Molecules not only having alkoxysilane groups but also comprising isocyanate groups offer the option of introducing the functionalities that result as reaction products, siloxanes and polyurethane groups, through one component. Such substances have long been in use, for example in the form of isocyanatoalkyltrialkoxysilanes.

Alkoxysilane-terminated polyurethanes produced from isocyanatoalkyltrialkoxysilanes and alcohols are also known and are used, for example, for producing highly crosslinked, hard coating materials (e.g. EP 2676982 A1). The alkoxysilane-containing coating materials described in EP 2676982 A1, however, are disadvantageous in having only short potlives.

Allophanate-containing binders are known. Alkoxysilane-functionalized allophanates are also known. It is appropriate here to distinguish between various types, which are set out below, but which correspond neither in structure nor in application to alkoxysilane-functionalized allophanates present in the alkoxysilane- and allophanate-functionalized binder according to the invention.

For instance, the allophanates III (1) described in WO 2008/043722 A1 are obtained by reacting NCO-terminated allophanate-containing polyurethanes I (1) with isocyanate-reactive alkoxysilanes II (1) (e.g. aminoalkyltrialkoxysilane). The allophanate groups here are therefore in the centre of the polyurethane chain and the alkoxysilane function is attached via the terminal isocyanate group in the context of a urea function (structure III (1), equation 1).

(Equation 1)

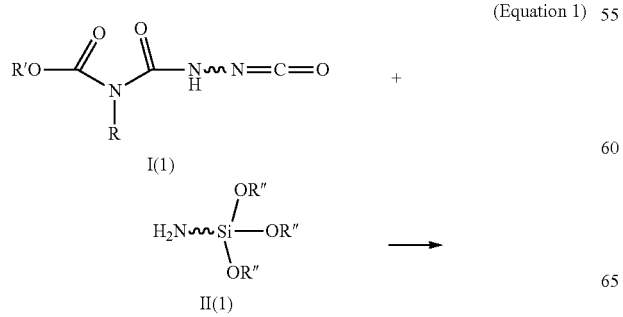

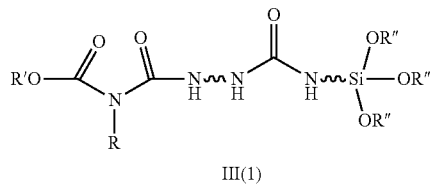

DE 102005041953 A1 describes the reaction of a polyol I (2) having an average molecular weight of 3000-20 000 g/mol with an excess of isocyanatopropyltrimethoxysilane II (2) so that after polyurethane formation III (2) an allophanate IV (2) having two alkoxysilane functions per allophanate unit is formed.

(Equation 2)

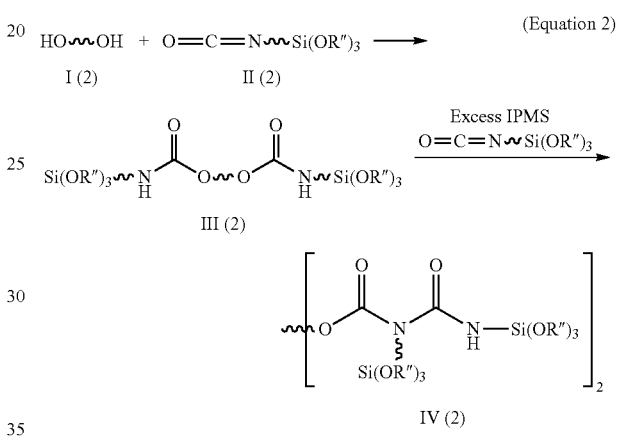

In DE 102005041954 A1, a polyurethane I (3) is admixed with isocyanatopropyltrimethoxysilane II (3) and the mixture is heated until allophanate structures are formed. In this case, the alkoxysilane group is added onto the terminal nitrogen of the allophanate group III (3) (equation 3).

(Equation 3)

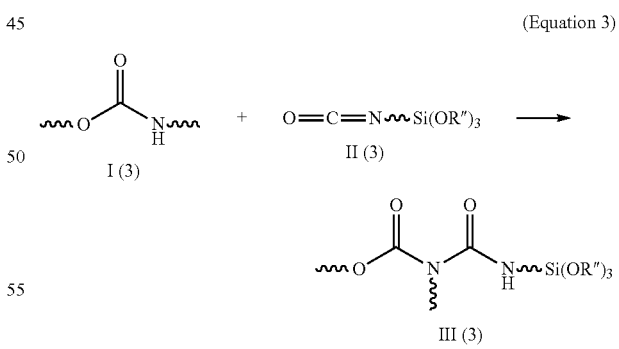

J. Kozakiewicz et al. published, in *Progress in Organic Coatings* 72 (2011) 120-130, the reaction of isocyanatopropyltrimethoxysilane I (4) with methanol to form the corresponding urethane II (4) and subsequently with hexamethylene diisocyanate trimer III (4). In the highly viscous allophanate IV (4) resulting therefrom, the alkoxysilane function is attached to the tertiary, central amine of the allophanate group (equation 4).

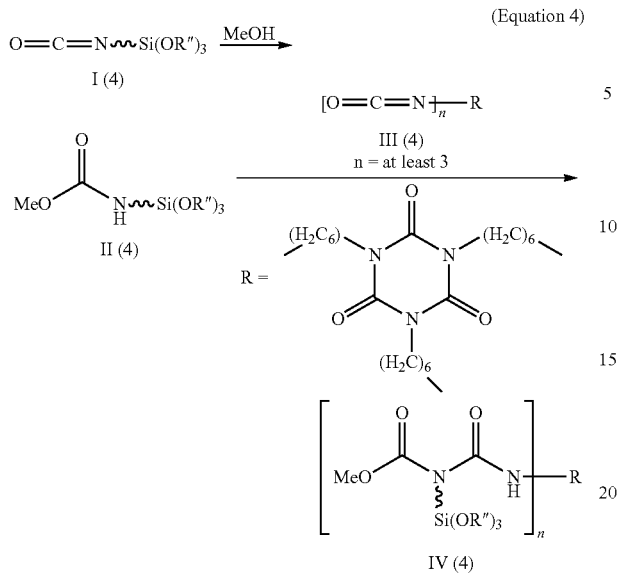

(Equation 4)

In the described application, the allophanate function serves as blocking agent for the hexamethylene diisocyanate trimer used as a crosslinker for hydroxy-functionalized polyester polyols.

Even today there is a need for new silane-containing coating materials having specific properties.

SUMMARY

The present invention has for its object to provide novel silane-containing coating materials which are suitable for the development of highly crosslinked, hard yet nevertheless flexible coatings and feature extended potlife.

This object is achieved by alkoxysilane- and allophanate-functionalized coating materials according to the present invention.

It has been found that, surprisingly, the alkoxysilane-functionalized, allophanate-containing coating materials according to the invention are suitable for use as paint, adhesive or sealant. In particular, the alkoxysilane- and allophanate-functionalized coating materials according to the invention may be used for developing highly crosslinked, particularly hard coatings having high flexibility. In addition, the alkoxysilane- and allophanate-functionalized coating materials according to the invention comprising the binder component a) according to the invention, which is an alkoxysilane- and allophanate-functionalized urethane, feature a long potlife.

DETAILED DESCRIPTION

The invention provides alkoxysilane-functionalized and allophanate-functionalized coating materials comprising
a) a binder component of 10-99 wt % of at least one reaction product of
I.
A) at least one, preferably one, alkoxysilane-containing monourethane A) of the formula 1

$R_n(OR^1)_{3-n}Si-R^2-NH-(C=O)-OR^3$    formula 1 wherein R, $R^1$, $R^2$ and $R^3$ independently of one another represent hydrocarbon radicals having 1-8 carbon atoms, wherein these may be linear, branched or cyclic or else may be integrated together to form a cyclic system, and n represents 0-2,
and
B) at least one diisocyanate B),
optionally in the presence of at least one catalyst K),
in a molar ratio of A) to B) of 1.0:1.5 to 1.0:0.6, preferably 1.15:1 to 0.85:1, particularly preferably of 1:1.
II.
and subsequent reaction
C) with at least one diol and/or polyol C),
optionally in the presence of at least one catalyst K),
in a ratio of NCO groups of reaction product I. to OH groups of the diol and/or polyol II. C) of 1.0:1.5 to 1.0:0.6, preferably 1.15:1 to 0.85:1, particularly preferably 1:1,
b) 1-90 wt % of at least one further binder component distinct from a), preferably of a hydroxyl-containing or amino-containing binder component,
c) 0-50 wt % of at least one aromatic, aliphatic or cycloaliphatic polyisocyanate having an NCO functionality of at least 2, preferably 2.8 to 6,
d) 0-5 wt % of at least one catalyst,
wherein components a)-d) add up to 100 wt %,
e) optionally auxiliaries and/or additives,
f) optionally solvents.

The allophanate-functionalized coating materials according to the invention are coating materials comprising at least reaction product which is an adduct of at least one monourethane with at least one diisocyanate that has been reacted with a diol and/or polyol.

As is apparent from the reaction of at least one monourethane with at least one diisocyanate in the molar ratio of 1.0:1.5 to 1.0:0.6, preferably 1.15:1 to 0.85:1, the adducts formed in step I. are adducts having on average 0.6-1.5 allophanate units, since the diisocyanate can undergo partial or complete reaction with one or two monourethanes. It is preferable, however, when the adduct according to the invention has on average one, preferably one, allophanate unit.

The adduct is then reacted with at least one diol and/or polyol to react hitherto unreacted isocyanate groups. It is preferable to react a 1:1 adduct of monourethane and diisocyanate, which thus still has one free isocyanate group, with the at least one diol/polyol.

It is particularly preferable when the alkoxysilane-functionalized and allophanate-functionalized urethane according to the invention is an adduct of one monourethane and one diisocyanate which has subsequently been reacted with one diol/polyol to give an adduct having one allophanate and one urethane unit.

"One" monourethane, "one" diisocyanate, "one" diol or "one" polyol is in particular to be understood as meaning in each case the respective monourethane, diisocyanate, diol or polyol of an empirical formula.

The term "binder component" may preferably be understood as meaning binders and crosslinkers, particularly preferably binders.

The invention also provides alkoxysilane-functionalized and allophanate-functionalized coating materials consisting of
a) a binder component of 10-99 wt % of at least one reaction product of
I.
A) at least one, preferably one, alkoxysilane-containing monourethane A) of the formula 1

$R_n(OR^1)_{3-n}Si-R^2-NH-(C=O)-OR^3$    formula 1 wherein R, R¹, R² and R³ independently of one another represent hydrocarbon radicals having 1-8 carbon atoms, wherein these may be linear, branched or cyclic or else may be integrated together to form a cyclic system, and n represents 0-2,
and
B) at least one diisocyanate B),
optionally in the presence of at least one catalyst K),
in a molar ratio of A) to B) of 1.0:1.5 to 1.0:0.6, preferably 1.15:1 to 0.85:1, particularly preferably of 1:1.

II.
and subsequent reaction
C) with at least one diol and/or polyol C),
optionally in the presence of at least one catalyst K),
in a ratio of NCO groups of reaction product I. to OH groups of the diol and/or polyol II. C) of 1.0:1.5 to 1.0:0.6, preferably 1.15:1 to 0.85:1, particularly preferably 1:1;
b) 1-90 wt % of at least one further binder component distinct from a), preferably of a hydroxyl-containing or amino-containing binder,
c) 0-50 wt % of at least one aromatic, aliphatic or cycloaliphatic polyisocyanate having an NCO functionality of at least 2, preferably 2.8 to 6,
d) 0-5 wt % of at least one catalyst,
wherein components a)-d) add up to 100 wt %,
e) optionally auxiliaries and/or additives,
f) optionally solvents.

It is preferable when R, R¹, R² and R³ are simultaneously or independently of one another methyl, ethyl, n-propyl, isopropyl, n-butyl, sec-butyl or tert-butyl.

It is preferable when n=0.

It is preferable when R¹ and R³ are simultaneously or independently of one another methyl or ethyl.

R² is preferably methyl or propyl.

Preference is given to compounds having n equal to 0, R¹ and R³ simultaneously or independently of one another equal to methyl or ethyl and R² simultaneously or independently of one another equal to methyl or propyl.

Preferably, R³=R¹.

Preference is given to compounds having n equal to 0 and R² equal to methyl or propyl, and R¹ equal to methyl or ethyl and R³=R¹.

Very particular preference is given to the compound having n equal to 0, R¹ and R³ equal to methyl and R² equal to propyl, N-trimethoxysilylpropylmethylcarbamate.

The diisocyanate B) employed in accordance with the invention may be any aromatic, aliphatic, cycloaliphatic and/or (cyclo)aliphatic diisocyanate. In a preferred embodiment the term "(cyclo)aliphatic diisocyanate" as used herein is to be understood as meaning that one molecule simultaneously comprises NCO groups bonded to a ring and NCO groups bonded to an aliphatic radical as is the case, for example, for isophorone diisocyanate. In a preferred embodiment the term "cycloaliphatic diisocyanate" as used herein is to be understood as meaning a diisocyanate which comprises only NCO groups bonded directly to the cycloaliphatic ring, an example being diisocyanatodicyclohexylmethane (H12MDI).

Suitable aromatic diisocyanates B) in principle include all known aromatic compounds. Particularly suitable are phenylene 1,3- and 1,4-diisocyanate, naphthylene 1,5-diisocyanate, tolylene 2,6-diisocyanate (2,6-TDI), tolylene 2,4-diisocyanate (2,4-TDI), diphenylmethane 2,4'-diisocyanate (2,4'-MDI), diphenylmethane 4,4'-diisocyanate (4,4'-MDI), the mixtures of monomeric diphenylmethane diisocyanates (MDI) and oligomeric diphenylmethane diisocyanates (polymer MDI), xylylene diisocyanate (MXDI) and tetramethylxylylene diisocyanate (TMXDI).

Aliphatic diisocyanates suitable for use as diisocyanate B) comprise linear and/or branched alkylene radicals having preferably 3 to 16 carbon atoms, more preferably 4 to 12 carbon atoms. Suitable cycloaliphatic or (cyclo)aliphatic diisocyanates comprise a cycloalkylene radical having preferably 4 to 18 carbon atoms, more preferably 6 to 15 carbon atoms. Examples of suitable diisocyanates include cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, such as 4-isocyanatomethyl-1,8-octane diisocyanate (TIN), decane di- and triisocyanate, undecane di- and triisocyanate, dodecane di- and triisocyanates. Likewise suitable are 4-methylcyclohexane 1,3-diisocyanate, 2-butyl-2-ethylpentamethylene diisocyanate, 3(4)-isocyanatomethyl-1-methylcyclohexyl isocyanate, 2-isocyanatopropylcyclohexyl isocyanate, 2,4'-methylenebis(cyclohexyl) diisocyanate and/or 1,4-diisocyanato-4-methylpentane.

Preferred diisocyanates B) are isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), individually or in admixture.

In a particularly preferred embodiment the diisocyanate B) is IPDI and/or 4,4'-H12MDI and/or HDI and/or a mixture of 2,2,4-TMDI and 2,4,4-TMDI.

Diols C) and polyols C) employed are, for example, ethylene glycol, propane-1,2-diol, propane-1,3-diol, diethylene glycol, dipropylene glycol, triethylene glycol, tetraethylene glycol, butane-1,2-diol, butane-1,4-diol, butylethylpropane-1,3-diol, methylpropane-1,3-diol, pentane-1,5-diol, bis(1,4-hydroxymethyl)cyclohexane (cyclohexanedimethanol), glycerol, hexanediol, neopentyl glycol, trimethylolethane, trimethylolpropane, pentaerythritol, bisphenol A, bisphenol B, bisphenol C, bisphenol F, norbornylene glycol, 1,4-benzyldimethanol, 1,4-benzyldiethanol, 2,4-dimethyl-2-ethylhexane-1,3-diol, 1,4-butylene glycol, 2,3-butylene glycol, di-β-hydroxyethylbutanediol, pentane-1,5-diol, hexane-1,6-diol, octane-1,8-diol, decanediol, dodecanediol, neopentyl glycol, cyclohexanediol, 3(4),8(9)-bis(hydroxymethyl)tricyclo[5.2.1.0$^{2,6}$]decane (dicidol), 2,2-bis(4-hydroxycyclohexyl)propane, 2,2-bis[4-(β-hydroxyethoxy)phenyl]propane, 2-methylpropane-1,3-diol, 2-methylpentane-1,5-diol, 2,2,4(2,4,4)-trimethylhexane-1,6-diol, hexane-1,2,6-triol, butane-1,2,4-triol, 2,2-dimethylpropane-1,3-diol, heptane-1,7-diol, octadecene-9,10-diol-(1,12), thiodiglycol, octadecane-1,18-diol, 2,4-dimethyl-2-propylheptane-1,3-diol, tris(β-hydroxyethyl) isocyanurate, mannitol, sorbitol, polypropylene glycols, polybutylene glycols, xylylene glycol or neopentyl glycol hydroxypivalate, alone or in admixture.

Particularly preferred diols C) and polyols C) are ethylene glycol, triethylene glycol, butane-1,4-diol, propane-1,2-diol, pentane-1,5-diol, hexane-1,6-diol, cyclohexanedimethanol, decanediol, dodecane-1,12-diol, 2,2,4-trimethylhexane-1,6- diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, trimethylolpropane, 2,2-dimethylpropane-1,3-diol (neopentyl glycol), neopentyl glycol hydroxypivalate and cis/trans-cyclohexane-1,4-diol, alone or in admixture.

Very particularly preferred diols C) and polyols C) are pentane-1,5-diol, hexane-1,6-diol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, 2,2-dimethylpropane-1,3-diol (neopentyl glycol) and cis/trans-cyclohexane-1,4-diol, alone or in admixture.

As component C), preference is given to using hydroxyl-containing polyesters, polyethers, polyacrylates, polycarbonates and polyurethanes having an OH number of 20 to 500 mg KOH/g and an average molar mass of 250 to 6000 g/mol. It is particularly preferable in the context of the present invention to use hydroxyl-containing polyesters or polyacrylates having an OH number of 50 to 250 mg KOH/g and an average molecular weight of 500 to 6000 g/mol. The hydroxyl number (OH number, OHN) is determined in accordance with DIN 53240-2. In this method the sample is reacted with acetic anhydride in the presence of 4-dimethylaminopyridine as catalyst to acetylate the hydroxyl groups. This forms one molecule of acetic acid per hydroxyl group while the subsequent hydrolysis of the excess acetic anhydride yields two molecules of acetic acid. The consumption of acetic acid is determined by titrimetry from the difference between the main value and a blank value, which is to be carried out in parallel. The molecular weight is determined by means of gel permeation chromatography (GPC). The samples are characterized in tetrahydrofuran as eluent in accordance with DIN 55672-1.

Hydroxyl-containing (meth)acrylic copolymers employable as component C) may be resins having a monomer composition of the kind described, for example, in WO 93/15849 (page 8, line 25 to page 10, line 5). The acid number of the (meth)acrylic copolymer to be established by employing a proportion of (meth)acrylic acid as monomer should be 0 to 30, preferably 0 to 15 mg KOH/g. The number-average molar weight (determined by gel permeation chromatography against a polystyrene standard) of the (meth)acrylic copolymer is preferably 2000 to 20 000 g/mol, the glass transition temperature is preferably −40° C. to +60° C. and the hydroxyl content of the (meth)acrylic copolymers for use according to the invention which is to be established by employing a proportion of hydroxyalkyl (meth)acrylates is preferably 20 to 500 mg KOH/g, more preferably 50 to 250 mg KOH/g.

Polyester polyols suitable as component C) in accordance with the invention are resins having a monomer composition composed of dicarboxylic and polycarboxylic acids and diols and polyols, such as are described in WO 93/15849. Also employable as polyester polyols are polyaddition products of caprolactone onto low molecular weight di- and triols such as are available under the trade name CAPA® (Perstorp) for example. The arithmetically determined number-average molar weight is preferably 500 to 5000 g/mol, particularly preferably 800 to 3000 g/mol; the average functionality is preferably 2.0 to 4.0, by preference 2.0 to 3.5.

Urethane- and ester-containing polyols employable in accordance with the invention as component C) also include in principle those described in EP 140 186. Preference is given to using urethane- and ester-containing polyols which are produced using HDI, IPDI, trimethylhexamethylene diisocyanate (TMDI) or dicyclohexylmethane diisocyanate (H12MDI). The number-average molar weight is preferably 500-5000 g/mol; the average functionality is in particular in the range of 2.0-3.5.

Suitable components C) are diols and polyols comprising further functional groups. These are the familiar linear or branched hydroxyl-containing polyesters, polycarbonates, polycaprolactones, polyethers, polythioethers, polyesteramides, polyurethanes or polyacetals. Their number-average molecular weight is preferably in the range from 134 to 3500 g/mol. Preference is given to linear hydroxyl-containing polyesters—polyester polyols—or mixtures of such polyesters. They are produced, for example, by reaction of diols with substoichiometric amounts of dicarboxylic acids, corresponding dicarboxylic anhydrides, corresponding dicarboxylic esters of lower alcohols, lactones or hydroxycarboxylic acids.

Diols suitable for producing the polyester polyols also include, in addition to the abovementioned diols, 2-methylpropanediol, 2,2-dimethylpropanediol, diethylene glycol, dodecane-1,12-diol, cyclohexane-1,4-dimethanol and cyclohexane-1,2- and -1,4-diol.

Dicarboxylic acids or derivatives suitable for producing the polyester polyols may be aliphatic, cycloaliphatic, aromatic and/or heteroaromatic in nature and optionally substituted, for example by halogen atoms, and/or unsaturated.

The preferred dicarboxylic acids or derivatives include succinic acid, adipic acid, suberic acid, azelaic acid, sebacic acid, 2,2,4(2,4,4)-trimethyladipic acid, phthalic acid, phthalic anhydride, isophthalic acid, terephthalic acid, dimethyl terephthalate, tetrahydrophthalic acid, maleic acid, maleic anhydride and dimeric fatty acids.

Suitable polyester polyols further include those which may be produced in known fashion by ring opening from lactones, such as epsilon-caprolactone, and simple diols as starter molecules.

The diols and dicarboxylic acids/derivatives thereof used for producing the polyester polyols may be used in any desired mixtures.

It will be appreciated that it is also possible to employ mixtures of the components C) described above.

The ratio of NCO groups of reaction product I. to OH groups of the diol and/or polyol II. C) varies from 1.0:1.5 to 1.0:0.6, preferably 1.15:1 to 0.85:1, particularly preferably 1:1.

The production of the alkoxysilane-functionalized and allophanate-functionalized binder components a) according to the invention is effected in two steps. In step I. the monourethane A) is reacted with the diisocyanate B), which results in the reaction product I. Subsequently step II. is carried out in which the reaction product I. is reacted with diols and/or polyols to form urethane functions.

In general, step I. and II. are carried out without solvent or using aprotic solvents and the reaction can be carried out batchwise or continuously. The reactions of step I. and II. are carried out in suitable equipment, e.g. stirred tanks, extruders, static mixers, kneading chambers. The reactions of step I. and II. can be conducted at room temperature, i.e. at temperatures in the range from 15° C. to 40° C., in particular in the range from 15° C. to 25° C. Preferably, however, higher temperatures are used, in the 80° C. to 220° C. range, in particular in the range from 80° C. to 120° C. The reactions of step I. and II. are carried out with exclusion of water. The reactions of step I. and II. are preferably carried out without solvent.

To accelerate the reactions of step I. and II., it is advantageously possible to use catalysts K) known in urethane chemistry, for example organometallic compounds, such as compounds containing tin or zinc, salts, for example Zn(II) chloride, and/or bases. Suitable for example are carboxylates of Sn, Bi, Zn and other metals, for example dibutyltin dilaurate, tin octoate, zinc (II) ethylhexanoate, bismuth neodecanoate, tertiary amines such as, for example, 1,4-diazabicyclo[2.2.2]octane (DABCO), 1,8-diazabicyclo[5.4.0]undec-7-ene (DBU), 1,5-diazabicyclo[4.3.0]non-5-ene (DBN), triethylamine, amidines and guanidines, and also quaternary ammonium salts, preferably tetraalkylammonium salts, and/or quaternary phosphonium salts.

Useful catalysts K) also include metal acetylacetonates. Examples thereof are zinc acetylacetonate, lithium acetylacetonate, iron acetylacetonate and tin acetylacetonate, alone or in admixture. Useful catalysts also include quaternary ammonium acetylacetonates or quaternary phosphonium acetylacetonates.

For the reaction of step I. preference is given to using zinc acetylacetonate or zinc ethylhexanoate.

The catalysts employable in step I. and II. may be identical or different.

The coating material according to the invention comprises as component b) at least one further binder component distinct from a). Suitable in principle as binders are all kinds of binders known to the skilled person, including, for example, binders which are thermoplastic, in other words not crosslinkable, which customarily have an average molecular weight>10 000 g/mol. Preferred binders, however, are those which possess reactive functional groups having acidic hydrogen atoms, examples being hydroxyl or primary or secondary amine groups. Suitable binders of the recited type have for example at least one, but preferably two or more, hydroxyl group(s). Further suitable functional groups of the binder are alkoxysilane functionalities, for example.

As binder component b) having functional groups, preference is given to using hydroxyl-containing polyesters, polyethers, polyacrylates, polycarbonates and polyurethanes having an OH number of 20 to 500 mg KOH/g and an average molar mass of 250 to 6000 g/mol. Particular preference in the context of the present invention is given to using hydroxyl-containing polyesters or polyacrylates having an OH number of 50 to 250 mg KOH/g and an average molecular weight of 500 to 6000 g/mol as binder components. The hydroxyl number (OH number, OHN) is determined in accordance with DIN 53240-2. In this method the sample is reacted with acetic anhydride in the presence of 4-dimethylaminopyridine as catalyst to acetylate the hydroxyl groups. This forms one molecule of acetic acid per hydroxyl group while the subsequent hydrolysis of the excess acetic anhydride yields two molecules of acetic acid. The consumption of acetic acid is determined by titrimetry from the difference between the main value and a blank value, which is to be carried out in parallel. The molecular weight is determined by means of gel permeation chromatography (GPC). The samples are characterized in tetrahydrofuran as eluent in accordance with DIN 55672-1.

Hydroxyl-containing (meth)acrylic copolymers employable as binder component b) may be resins having a monomer composition of the kind described, for example, in WO 93/15849 A1 (page 8, line 25 to page 10, line 5). The acid number of the (meth)acrylic copolymer to be established by employing a proportion of (meth)acrylic acid as monomer should be 0 to 30, preferably 0 to 15 mg KOH/g. The number-average molar weight (determined by gel permeation chromatography against a polystyrene standard) of the (meth)acrylic copolymer is preferably 2000 to 20 000 g/mol; the glass transition temperature is preferably −40° C. to +60° C. The hydroxyl content of the (meth)acrylic copolymers for use in accordance with the invention to be established by employing a proportion of hydroxyalkyl (meth)acrylates is preferably 20 to 500 mg KOH/g, particularly preferably 50 to 250 mg KOH/g.

Polyester polyols suitable as binder component b) in accordance with the invention are resins having a monomer composition composed of dicarboxylic and polycarboxylic acids and diols and polyols, such as are described in WO 93/15849 A1. Also employable as polyester polyols are polyaddition products of caprolactone onto low molecular weight di- and triols such as are available under the trade name CAPA® (Perstorp) for example. The arithmetically determined number-average molar weight is preferably 500 to 5000 g/mol, particularly preferably 800 to 3000 g/mol; the average functionality is preferably 2.0 to 4.0, by preference 2.0 to 3.5.

Urethane- and ester-containing polyols employable in accordance with the invention as binder component b) also include in principle those described in EP 140 186 A1. Preference is given to using urethane- and ester-containing polyols which are produced using HDI, IPDI, trimethylhexamethylene diisocyanate (TMDI) or dicyclohexylmethane diisocyanate (H12MDI).

The number-average molar weight is preferably 500-5000 g/mol; the average functionality is in particular in the range of 2.0-3.5.

Trialkoxysilane-functional binders too are suitable for use as component b). Such resins are obtainable by copolymerization of acrylate or methacrylate monomers with acryloyl- or methacryloyl-functional alkyltrialkoxysilane derivatives (for example Dynasylan® MEMO from Evonik Industries AG) as are described, for example, in WO 92/11328. An alternative synthesis route comprises derivatization of hydroxyl-containing polyethers, polyesters, polycarbonate diols or polyacrylates with isocyanatopropyltrialkoxysilane as is described, for example, in Examples 3 and 4 of WO2008/131715. Also useful are amino-containing binders, for example aminopropyltrimethoxysilane (e.g. Dynasylan AMMO from Evonik Industries AG), aminopropyltriethoxysilane, aminomethyltrimethoxysilane or aminomethyltriethoxysilane.

It will be appreciated that it is also possible to employ mixtures of the binder components b) described hereinabove.

Particularly preferred binder components b) are hydroxyl-containing polyesters and polyacrylates, alone or in admixture.

The proportion of the binder component b) in the binder according to the invention is preferably 1 to 90 weight percent, based on the sum of the components a), b) and optionally c) and d), preferably 20 to 60 weight percent.

Component c)

The polyisocyanates c) used in accordance with the invention may consist of any desired aromatic, aliphatic, cycloaliphatic and/or (cyclo)aliphatic polyisocyanates.

Suitable aromatic polyisocyanates c) are in principle any known aromatic compounds. Particularly suitable are phenylene 1,3- and 1,4-diisocyanate, naphthylene 1,5-diisocyanate, tolylene 2,6-diisocyanate (2,6-TDI), tolylene 2,4-diisocyanate (2,4-TDI), diphenylmethane 2,4'-diisocyanate (2,4'-MDI), diphenylmethane 4,4'-diisocyanate (4,4'-MDI), the mixtures of monomeric diphenylmethane diisocyanates (MDI) and oligomeric diphenylmethane diisocyanates (polymer MDI), xylylene diisocyanate (MXDI) and tetramethylxylylene diisocyanate (TMXDI).

The aliphatic or cycloaliphatic polyisocyanate c) used as crosslinker component c) comprises at least one aliphatic and/or cycloaliphatic polyisocyanate having an NCO functionality of at least 2, preferably 2 to 6, more preferably from 2.8 to 6, most preferably 2 to 4. The term "NCO functionality" as used herein is to be understood as meaning the number of reactive NCO substituents comprised on average by the molecule in question, preferably the crosslinker component c).

The polyisocyanate c) used in accordance with the invention as inventive component c) may be any aliphatic, cycloaliphatic and/or (cyclo)aliphatic diisocyanate. (Cyclo)aliphatic diisocyanates are well understood by the skilled person as meaning simultaneously cyclically and aliphatically bonded NCO groups, as is the case with isophorone diisocyanate for example. By contrast, cycloaliphatic diisocyanates are understood as meaning diisocyanates having only NCO groups bonded directly to the cycloaliphatic ring, for example H12MDI.

Aliphatic polyisocyanates suitable for use as inventive component c) comprise a linear or branched alkylene radical having preferably 3 to 16 carbon atoms, more preferably 4 to 12 carbon atoms. Suitable cycloaliphatic or (cyclo)aliphatic polyisocyanates c) comprise a cycloalkylene radical having preferably 4 to 18 carbon atoms, more preferably 6 to 15 carbon atoms. Examples of suitable di- or polyisocyanates include cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, nonane triisocyanate, such as 4-isocyanatomethyl-1,8-octane diisocyanate (TIN), decane di- and triisocyanate, undecane di- and triisocyanate, dodecane di- and triisocyanates. Likewise suitable are 4-methylcyclohexane 1,3-diisocyanate, 2-butyl-2-ethylpentamethylene diisocyanate, 3(4)-isocyanatomethyl-1-methylcyclohexyl isocyanate, 2-isocyanatopropylcyclohexyl isocyanate, 2,4'-methylenebis(cyclohexyl) diisocyanate and/or 1,4-diisocyanato-4-methylpentane.

The polyisocyanate used as inventive component c) is preferably selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), individually or in admixture.

The polyisocyanate used as inventive component c) is particularly preferably selected from the group comprising isophorone diisocyanate (IPDI), hexamethylene diisocyanate (HDI), diisocyanatodicyclohexylmethane (H12MDI), 2-methylpentane diisocyanate (MPDI), 2,2,4-trimethylhexamethylene diisocyanate/2,4,4-trimethylhexamethylene diisocyanate (TMDI), norbornane diisocyanate (NBDI). Particular preference is given to IPDI, HDI, TMDI and/or H12MDI, with IPDI, H12MDI and/or HDI representing the most preferred polyisocyanates.

Also used with preference as inventive component c) are polyisocyanates which can be produced from the recited diisocyanates or mixtures thereof by linking by means of urethane, allophanate, urea, biuret, uretdione, amide, isocyanurate, carbodiimide, uretonimine, oxadiazinetrione or iminooxadiazinedione structures. Such polyisocyanates are commercially available. Particularly preferred as inventive component c) are isocyanurates, in particular isocyanurates of IPDI and/or HDI, for example VESTANAT HT 2500 L and VESTANAT T 1890. Polyisocyanates of this kind may in addition optionally be chain-extended or branched with di- or polyfunctional H acidic components, for example di- or polyols and/or di- or polyamines.

Particularly preferred for use as components c) according to the invention are isocyanurates freed of residual monomers by distillative removal, to give a polyisocyanate residual monomer content of <0.5 wt %.

Any desired mixtures of the above-described diisocyanates and/or polyisocyanates may be used in the context of the present invention.

Component c), if present, is present in the coating material according to the invention in an amount of 5 to 50 weight percent, preferably 15 to 40 weight percent, based on the sum of the components a), b), optionally c) and d).

In a preferred embodiment catalyst d) is present in the coating material according to the invention in an amount of 0.1 up to 5 weight percent, preferably 0.2 to 3 weight percent, based on the sum of the components a), b), optionally c) and d).

Catalysts d) used may be organic carboxylic acids. Examples of suitable carboxylic acids are, in particular, salicylic acid, benzoic acid, citric acid, phthalic acid, terephthalic acid, isophthalic acid, dodecanoic acid, 1,12-dodecanedioic acid and/or ascorbic acid. Preference is given to using salicylic acid, citric acid or benzoic acid, and mixtures of the stated carboxylic acids may also be employed.

Also employable as catalyst d) are quaternary ammonium salts, alone or in admixture, preferably tetraalkylammonium salts and/or quaternary phosphonium salts with halogens, hydroxides, alkoxides or organic or inorganic acid anions as a counterion. Examples of these are: tetramethylammonium formate, tetramethylammonium acetate, tetramethylammonium propionate, tetramethylammonium butyrate, tetramethylammonium benzoate, tetraethylammonium formate, tetraethylammonium acetate, tetraethylammonium propionate, tetraethylammonium butyrate, tetraethylammonium benzoate, tetrapropylammonium formate, tetrapropylammonium acetate, tetrapropylammonium propionate, tetrapropylammonium butyrate, tetrapropylammonium benzoate, tetrabutylammonium formate, tetrabutylammonium acetate, tetrabutylammonium propionate, tetrabutylammonium butyrate and tetrabutylammonium benzoate, and tetrabutylphosphonium acetate, tetrabutylphosphonium formate and ethyltriphenylphosphonium acetate, tetrabutylphosphonium benzotriazolate, tetraphenylphosphonium phenolate and trihexyltetradecylphosphonium decanoate, methyltributylammonium hydroxide, methyltriethylammonium hydroxide, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, tetradecylammonium hydroxide, tetradecyltrihexylammonium hydroxide, tetraoctadecylammonium hydroxide, benzyltrimethylammonium hydroxide, benzyltriethylammonium hydroxide, trimethylphenylammonium hydroxide, triethylmethylammonium hydroxide, trimethylvinylammonium hydroxide, methyltributylammonium methoxide, methyltriethylammonium methoxide, tetramethylammonium methoxide, tetraethylammonium methoxide, tetrapropylammonium methoxide, tetrabutylammonium methoxide, tetrapentylammonium methoxide, tetrahexylammonium methoxide, tetraoctylammonium methoxide, tetradecylammonium methoxide, tetradecyltrihexylammonium methoxide, tetraoctadecylammonium methoxide, benzyltrimethylammonium methoxide, benzyltriethylammonium methoxide, trimethylphenylammonium methoxide, triethylmethylammonium methoxide, trimethylvinylammonium methoxide, methyltributylammonium ethoxide, methyltriethylammonium ethoxide, tetramethylammonium ethoxide, tetraethylammonium ethoxide, tetrapropylammonium ethoxide, tetrabutylammonium ethoxide, tetrapentylammonium ethoxide, tetrahexylammonium ethoxide, tetraoctylammonium methoxide, tetradecylammonium ethoxide, tetradecyltrihexylammonium ethoxide, tetraoctadecylammonium ethoxide, benzyltrimethylammonium ethoxide, benzyltriethylammonium ethoxide, trimethylphenylammonium ethoxide, triethylmethylammonium ethoxide, trimethylvinylammonium ethoxide, methyltributylammonium benzylate, methyltriethylammonium benzylate, tetramethylammonium benzylate, tetraethylammonium benzylate, tetrapropylammonium benzylate, tetrabutylammonium benzylate, tetrapentylammonium benzylate, tetrahexylammonium benzylate, tetraoctylammonium benzylate, tetradecylammonium benzylate, tetradecyltrihexylammonium benzylate, tetraoctadecylammonium benzylate, benzyltrimethylammonium benzylate, benzyltriethylammonium benzylate, trimethylphenylammonium benzylate, triethylmethylammonium benzylate, trimethylvinylammonium benzylate, tetramethylammonium fluoride, tetraethylammonium fluoride, tetrabutylammonium fluoride, tetraoctylammonium fluoride, benzyltrimethylammonium fluoride, tetrabutylphosphonium hydroxide, tetrabutylphosphonium fluoride, tetrabutylammonium chloride, tetrabutylammonium bromide, tetrabutylammonium iodide, tetraethylammonium chloride, tetraethylammonium bromide, tetraethylammonium iodide, tetramethylammonium chloride, tetramethylammonium bromide, tetramethylammonium iodide, benzyltrimethylammonium chloride, benzyltriethylammonium chloride, benzyltripropylammonium chloride, benzyltributylammonium chloride, methyltributylammonium chloride, methyltripropylammonium chloride, methyltriethylammonium chloride, methyltriphenylammonium chloride, phenyltrimethylammonium chloride, benzyltrimethylammonium bromide, benzyltriethylammonium bromide, benzyltripropylammonium bromide, benzyltributylammonium bromide, methyltributyl ammonium bromide, methyltripropylammonium bromide, methyltriethylammonium bromide, methyltriphenylammonium bromide, phenyltrimethylammonium bromide, benzyltrimethylammonium iodide, benzyltriethylammonium iodide, benzyltripropylammonium iodide, benzyltributylammonium iodide, methyltributylammonium iodide, methyltripropylammonium iodide, methyltriethylammonium iodide, methyltriphenylammonium iodide and phenyltrimethylammonium iodide, methyltributylammonium hydroxide, methyltriethylammonium hydroxide, tetramethylammonium hydroxide, tetraethylammonium hydroxide, tetrapropylammonium hydroxide, tetrabutylammonium hydroxide, tetrapentylammonium hydroxide, tetrahexyl ammonium hydroxide, tetraoctylammonium hydroxide, tetradecylammonium hydroxide, tetradecyltrihexylammonium hydroxide, tetraoctadecylammonium hydroxide, benzyltrimethylammonium hydroxide, benzyltriethylammonium hydroxide, trimethylphenylammonium hydroxide, triethylmethylammonium hydroxide, trimethylvinylammonium hydroxide, tetramethylammonium fluoride, tetraethylammonium fluoride, tetrabutylammonium fluoride, tetraoctylammonium fluoride and benzyltrimethylammonium fluoride. These catalysts may be added alone or in mixtures. Preference is given to using tetraethylammonium benzoate and tetrabutylammonium hydroxide.

As catalyst d) it is also possible to use metal complexes with chelate ligands. The chelate ligands are organic compounds having at least two functional groups which are able to coordinate to metal atoms or metal ions. Use may be made, for example, of the aluminium- and zirconium-chelate complexes, as described in U.S. Pat. No. 4,772,672 A, for example, as catalyst. Preferred metal chelates are chelates based on zinc, lithium, tin, aluminium, zirconium, titanium and/or boron, for example aluminium ethyl acetoacetate, zirconium ethyl acetoacetate, zinc acetylacetonate, lithium acetylacetonate and tin acetylacetonate, alone or in mixtures. Preference is given to using zinc acetylacetonate.

Useful catalysts d) are also quaternary ammonium acetylacetonates or quaternary phosphonium acetylacetonates.

Examples of such catalysts are tetramethylammonium acetylacetonate, tetraethylammonium acetylacetonate, tetrapropylammonium acetylacetonate, tetrabutylammonium acetylacetonate, benzyltrimethylammonium acetylacetonate, benzyltriethylammonium acetylacetonate, tetramethylphosphonium acetylacetonate, tetraethylphosphonium acetylacetonate, tetrapropylphosphonium acetylacetonate, tetrabutylphosphonium acetylacetonate, benzyltrimethylphosphonium acetyl acetonate, benzyltriethylphosphonium acetylacetonate. Particular preference is given to using tetraethylammonium acetylacetonate and tetrabutylammonium acetylacetonate. It will be appreciated that mixtures of such catalysts may also be used.

Suitable catalyst d) further include aluminium, zirconium, titanium and/or boron alkoxides and/or esters thereof.

Also suitable as catalysts are basic substances, for example guanidines and amidines and tertiary amines. Examples of these are tetramethylguanidine, diazabicycloundecene (DBU), diazabicyclononene (DBN), and diazabicyclooctane (DABCO).

As catalyst d) it is also possible to catalyse the urethane reaction using catalysts which have proved their worth within the field of PU technology, examples being organic Sn(IV), Sn(II), Zn and Bi compounds, or organometallic catalysts, for example dibutyltin dilaurate, tin octoate, zinc ethylhexanoate, bismuth neodecanoate, or tertiary amines, for example 1,4-diazabicyclo[2.2.2]octane. However, according to the invention such catalysts for urethane reactions are used only in blends with other catalysts according to the invention. Preference is given to using zinc ethylhexanoate.

As catalyst d) it is also possible to use a phosphorus-containing catalyst, preferably a phosphorus- and nitrogen-containing catalyst. Mixtures of two or more different catalysts may also be used here. Examples of suitable phosphorus-containing catalysts are substituted phosphonic diesters and diphosphonic diesters, preferably from the group consisting of acyclic phosphonic diesters, cyclic phosphonic diesters, acyclic diphosphonic diesters and cyclic diphosphonic diesters. Such catalysts are described in DE-A 102005045228, for example.

As catalyst d) it is also possible with preference to use an amine-blocked phosphoric ester and with particular preference amine-blocked ethylhexyl phosphate and amine-blocked phenyl phosphate. Examples of amines with which the phosphoric esters are blocked are in particular tertiary amines, for example triethylamine. Particularly preferred for use for blocking the phosphoric esters are tertiary amines which exhibit high catalyst activity at curing temperatures of 100° C. to 160° C. Certain amine-blocked phosphoric acid catalysts are also available commercially (e.g. Nacure products from King Industries). An example of a particularly suitable catalyst is that based on an amine-blocked partial ester of phosphoric acid, under the designation Nacure 4167 from King Industries.

Also possible for use as catalyst d) are organic sulphonic acids in non-blocked or blocked form. A suitable sulphonic acid is in principle any organic sulphonic acid, preference being given to p-toluenesulphonic acid and dodecylbenzenesulphonic acid. For coating systems which crosslink thermally, i.e. above 100° C., these sulphonic acids may also be employed with preference in amine-neutralized form according to the invention. Also possible for use in accordance with the invention are latent, non-ionogenic sulphonic acid derivatives which release sulphonic acids only at above 100° C., such as adducts of sulphonic acids with epoxide-containing components, for example, as described in DE-A 23 56768. Salts of trifluoromethanesulphonic acid (triflates) too are suitable sulphonic acid-based catalysts.

It is preferable to employ catalysts d) selected from tetraethylammonium benzoate, tetrabutylammonium hydroxide, tetraethylammonium acetylacetonate, tetrabutylammonium acetylacetonate, dibutyltin dilaurate, zinc acetylacetonate, zinc ethylhexanoate.

The catalyst d) in the coating materials according to the invention may consist solely of the abovementioned alternatives, although any desired mixtures of the catalysts may also be used.

The coating material according to the invention may further comprise auxiliaries and/or additives e) that are known within coatings technology, such as stabilizers, light stabilizers, catalysts, additional crosslinkers, fillers, pigments, flow control agents or rheological assistants, such as "sag control agents", for example, microgels or pyrogenic silicon dioxide or else nanoparticles, as described for example in EP 1204701 B1, in typical concentrations. Component e) may further comprise additional crosslinkers as known within coatings chemistry, which are used, for example, in the form of melamine resins, benzoguanamine resins, carbamate-functional components or blocked polyisocyanates. If necessary, inorganic or organic colour and/or effect pigments customary in coatings technology may also be incorporated in component e) of the coating materials according to the invention.

In a preferred embodiment the coating material according to the invention is a pigment-free system, i.e. a clearcoat system. Component e) in this case may be included in the coating material according to the invention preferably in an amount of 0.5 up to 8 weight percent, more preferably 1 to 6 weight percent, based on the sum of the components a), b), optionally c) and d).

In another preferred embodiment, the coating material according to the invention is a coloured coating system. Pigments and fillers as component e) may in this case be included in the coating material according to the invention in an amount from 10 to 200 weight percent, based on the sum of the components a), b), optionally c) and d).

The coating material according to the invention may further comprise organic solvents as component f). Suitable solvents are, for example, ketones, alcohols, esters, or aromatics.

Component f) is present in the coating material according to the invention preferably in amounts from 20 up to 150 weight percent, yet more preferably 30 to 60 weight percent, based on the sum of the components a), b), optionally c) and d).

The coating materials according to the invention are produced by mixing of the components described above. The mixing may take place by means of mixers known to the skilled person, for example batchwise in stirred containers, dissolvers, bead mills, roller mills, etc., or else continuously using static mixers for example.

The invention also provides for the use of the alkoxysilane-functionalized, allophanate-containing coating materials in paint compositions and adhesive compositions and sealant compositions and metal-coating compositions.

The invention also provides for the use of the alkoxysilane-functionalized, allophanate-containing coating materials in coating compositions and paint compositions for metal, glass, plastic, wood, MDF (Middle Density Fibreboards) or leather substrates or other heat-resistant substrates.

The invention also provides for the use of the alkoxysilane-functionalized, allophanate-containing coating materials according to the invention in adhesive materials for bonding applications of metal, plastic, glass, wood, MDF or leather substrates or other heat-resistant substrates.

The invention likewise provides metal-coating compositions, in particular for car bodies, motorcycles and pedal cycles, parts of buildings and household appliances, wood-coating compositions, MDF coatings, glass-coating compositions, leather-coating compositions and plastic-coating compositions.

The present invention is further illustrated by the following non-limiting examples from which further features, embodiments, aspects and advantages of the present invention may be discerned.

Examples

Input Materials:
Vestanat® EP-UPMS: trimethoxysilylpropyl methylcarbamate (Evonik Resource Efficiency GmbH) Vestanat® IPDI: isophorone diisocyanate (Evonik Resource Efficiency GmbH)

Vestanat® TMDI: mixture of 2,2,4-trimethylhexamethylene diisocyanate (2,2,4-TMDI) and 2,4,4-trimethylhexamethylene diisocyanate (Evonik Resource Efficiency GmbH)

Vestanat® HT 2500/100: hexamethylene 1,6-diisocyanate, homopolymeric (isocyanurate type) (Evonik Resource Efficiency GmbH)

Vestanat® EP Cat 11 B: tetraethylammonium benzoate in butanol (Evonik Resource Efficiency GmbH)

Tegoglide® 410: slip and antiblocking additive based on a polyether siloxane copolymer (Evonik Resource Efficiency GmbH)

Vestanat® EP-M60: linear, short-chain silane-functionalized crosslinker (Evonik Resource Efficiency GmbH)

Vestanat® EP-M95: branched, short-chain silane-functionalized crosslinker (Evonik Resource Efficiency GmbH)

Vestanat® EP-M120: linear, long-chain silane-functionalized crosslinker (Evonik Resource Efficiency GmbH)

Setalux® 1760 VB-64: polyacrylate polyol, Nuplex Resins B.V.

Tinuvin® 292: sterically hindered amine, light stabilizer; BASF SE

Tinuvin® 900: UV absorber; BASF SE

1. Production of a)

Alkoxysilane- and Allophanate-Functionalized Urethane 1

36.9 g of Vestanat® EP-UPMS, 0.04 g of zinc(II) ethylhexanoate and 34.7 g of Vestanat® IPDI were charged to a three-necked flask fitted with a reflux condenser, blanketed with nitrogen and heated with stirring to 100° C. After heating for 12 hours, an NCO content of 9.33% was obtained. The obtained allophanate was cooled, admixed with 8.37 g of pentanediol and 0.01% DBTL and stirred at 60-65° C. for 17 h until an NCO content of <0.1% was achieved and, after about 3 h, 20 g of butyl acetate were added for viscosity reduction. The alkoxysilane- and allophanate-funcionalized urethane 1 thus obtained is a clear liquid having a viscosity of 3457 mPas (at 23° C.).

Alkoxysilane- and Allophanate-Functionalized Urethane 2

31.7 g of Vestanat® EP-UPMS, 0.04 g of zinc(II) ethylhexanoate and 29.8 g of Vestanat® IPDI were charged to a three-necked flask fitted with a reflux condenser, blanketed with nitrogen and heated with stirring to 100° C. After heating for 6 hours, an NCO content of 9.12% was obtained. The resulting allophanate was cooled, admixed with 13.5 g of dodecanediol and 0.01% DBTL and stirred at 60-65° C. for several hours until an NCO content of <0.1% was achieved and then, while still hot, 20 g of 1-MOP acetate were added for viscosity reduction. The alkoxysilane- and allophanate-funcionalized urethane 2 thus obtained is a clear liquid having a viscosity of 1902 mPas (at 23° C.).

2. Preparation of Clearcoats from the Alkoxysilane-Functionalized and Allophanate-Functionalized Coating Materials For the formulation of the inventive clearcoats and of the comparative examples the components of the compositions represented in Table 1 were mixed with one another immediately prior to processing.

The viscosity of the formulations, determined as the flow time in the DIN 4 cup at 23° C., was approximately 20 seconds.

Table 2 reports the potlives of compositions I-VI. The potlives were determined as follows: The liquid sample for determination (at least 70 ml) is introduced into a 100 ml glass vial and provided vertically with a metal pin; hanging at the end of the pin immersed in the sample is a circular metal plaque having a diameter of approximately 2 cm. The glass vial is provided with a perforated lid and the metal pin is clamped into the gelation time instrument (Techne Gelation Timer). The sample is now in a water tank set at room temperature (23° C.) (Lauda thermostat model BK2). The metal pin in the sample moves up and down in oscillation at a constant rhythm until the resistance of the sample is greater than the force of the gelation time instrument. In this case, the metal pin comes to a standstill; the sample is "gelled". The time which elapses between the start of the oscillating movement of the metal pin and the end thereof is reported on the display of the gelation instrument.

TABLE 2

Potlives of compositions I-V

| Clearcoat system | Potlife (h) |
| --- | --- |
| I | 19.5 |
| II | 20.8 |
| III (Comparative example) | 4.3 |
| IV (Comparative example) | 4.0 |
| V (Comparative example) | 2.0 |

From the potlives set out in Table 2 it is clearly evident that the inventive alkoxysilane- and allophanate-functionalized coating materials I and II have a markedly longer potlife than the Comparative Examples III-V. From the prior art (Comparative Examples III-V) there was no expectation that the potlife of the inventive alkoxysilane- and allophanate-functionalized coating materials I and II, which comprise the inventive alkoxysilane- and allophanate-functionalized urethanes 1-2, would be prolonged many times over.

Curing of the Clearcoats

To determine the mechanical characteristics, all paints were applied to phosphatized steel sheets (Chemetall Gardobond 26S/60/OC) with a 120 μm doctor blade and cured for 22 minutes at 160° C.

TABLE 1

Composition of the inventive clearcoats and comparative examples

| Item | | I | II | III Comparative | IV Comparative | V Comparative |
| --- | --- | --- | --- | --- | --- | --- |
| 1 | Alkoxysilane- and allophanate-functionalized urethane 1 | 28.78 | | | | |
| 2 | Alkoxysilane- and allophanate-functionalized urethane 2 | | 31.40 | | | |
| 3 | Comparative example: Vestanat ® EP-M95 | | | 26.79 | | |
| 4 | Comparative example: Vestanat ® EP-M60 | | | | 26 | |
| 5 | Comparative example: Vestanat ® EP-M120 | | | | | 53.2 |
| 6 | Setalux ® 1760 VB-64 (64% strength) | 35.97 | 37.25 | 41.85 | 40.6 | 41.6 |
| 7 | EP-CAT 11 B | 0.92 | 0.95 | 1.06 | 1.0 | 1.1 |
| 8 | TegoGlide 410 (10% in butyl acetate) | 0.50 | 0.49 | 0.48 | 0.49 | 0.5 |
| 9 | Tinuvin 292 | 0.23 | 0.24 | 0.27 | 0.26 | 0.27 |
| 10 | Tinuvin 900 (8% in xylene) | 2.88 | 2.98 | 3.34 | 3.25 | 3.33 |
| 11 | Butyl acetate/xylene (1:1) | 30.72 | 28.28 | 26.21 | 28.4 | 0 |

TABLE 3

Coat properties of the inventive alkoxysilane- and allophanate-functionalized coating materials I-III after curing at 160° C. (22 min)

| | Composition | | |
|---|---|---|---|
| | I | II | III |
| Pendulum hardness (König) [s] after 1 d | 182 | 202 | 147 |
| Erichsen cupping [mm] (EN ISO 1520) | 6.0 | 6.5 | 4.5 |
| MEK test [ASTM D 4752] (Double rubs, 1 kg applied weight) | >150 | >150 | >150 |

The coat properties of the coatings obtained using the inventive alkoxysilane- and allophanate-functionalized coating materials I and II show a high pendulum hardness compared to comparative example III coupled with exceptionally high flexibility and good MEK resistance.

The invention claimed is:

1. An alkoxysilane-functionalized and allophanate-functionalized coating material comprising
    a) a binder component of 10-99 wt % of at least one reaction product of
    one an alkoxysilane-containing monourethane A) of formula 1

$$R_n(OR^1)_{3-n}Si-R^2-NH-(C=O)-OR^3 \quad \text{formula 1}$$

wherein R, $R^1$, and $R^3$ independently of one another represent hydrocarbon radicals, and $R^2$ is a diradical, having 1-8 carbon atoms, wherein these may be linear, branched or cyclic or else may be integrated together to form a cyclic system, and n represents 0-2, and
    a diisocyanate B),
    optionally in the presence of at least one catalyst K),
    in a molar ratio of A) to B) of from 1.0:1.5 to 1.0:0.6, II,
    and subsequent reaction of the at least one reaction product
    with at least one diol and/or polyol C),
    in the presence of at least one catalyst K),
    in a ratio of NCO groups of reaction product to OH groups of the diol and/or polyol C) of from 1.0:1.5 to 1.0:0.6;
    b) from 1-90 wt % of a hydroxyl-containing or amino-containing binder component,
    c) from 0-50 wt % of at least one aromatic, aliphatic or cycloaliphatic polyisocyanate having an NCO functionality of at least 2,
    d) from 0-5 wt % of at least one catalyst,
    wherein a)-d) add up to 100 wt %,
    e) optionally auxiliaries and/or additives,
    f) optionally solvents.

2. The alkoxysilane-functionalized and allophanate-functionalized coating material according to claim 1, wherein R, $R^1$, and $R^3$ simultaneously or independently of one another represent methyl, ethyl, n-propyl, isopropyl, n-butyl, sec-butyl or tert-butyl.

3. The alkoxysilane-functionalized and allophanate-functionalized coating material according to claim 1, wherein n is equal to 0, $R^1$ and $R^3$ simultaneously or independently of one another are methyl or ethyl and $R^2$ is methylene or propylene.

4. The alkoxysilane-functionalized and allophanate-functionalized coating material according to claim 1, wherein n is equal to 0 and $R^2$ is methylene or propylene, $R^1$ is methyl or ethyl and $R^3=R^1$.

5. The alkoxysilane-functionalized and allophanate-functionalized coating material according to claim 1, wherein n is equal to 0, $R^1$ and $R^3$ are methyl and $R^2$ is propylene.

6. The alkoxysilane-functionalized and allophanate-functionalized coating material according to claim 1, wherein the diisocyanate B) is selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), or xylylene diisocyanate (MXDI), individually or in admixture.

7. The alkoxysilane-functionalized and allophanate-functionalized coating material according to claim 1, wherein the diol and/or polyol C) is selected from the group consisting of ethylene glycol, propane-1,2-diol, propane-1,3-diol, diethylene glycol, dipropylene glycol, triethylene glycol, tetraethylene glycol, butane-1,2-diol, butane-1,4-diol, butylethylpropane-1,3-diol, methylpropane-1,3-diol, pentane-1,5-diol, bis(1,4-hydroxymethyl)cyclohexane (cyclohexanedimethanol), glycerol, hexanediol, neopentyl glycol, trimethylolethane, trimethylolpropane, pentaerythritol, bisphenol A, bisphenol B, bisphenol C, bisphenol F, norbornylene glycol, 1,4-benzyldimethanol, 1,4-benzyldiethanol, 2,4-dimethyl-2-ethylhexane-1,3-diol, 1,4-butylene glycol, 2,3-butylene glycol, di-β-hydroxyethylbutanediol, hexane-1,6-diol, octane-1,8-diol, decanediol, dodecanediol, cyclohexanediol, 3(4),8(9)-bis(hydroxymethyl)tricyclo[5.2.1.0²˒⁶]decane (dicidol), 2,2-bis(4-hydroxycyclohexyl)propane, 2,2-bis[4-(β-hydroxyethoxy)phenyl]propane, 2-methylpropane-1,3-diol, 2-methylpentane-1,5-diol, 2,2,4(2,4,4)-trimethylhexane-1,6-diol, hexane-1,2,6-triol, butane-1,2,4-triol, tris(β-hydroxyethyl) isocyanurate, mannitol, sorbitol, polypropylene glycols, polybutylene glycols, xylylene glycol or neopentyl glycol hydroxypivalate, alone or in admixture.

8. The alkoxysilane-functionalized and allophanate-functionalized coating material according to claim 1, wherein the diol and/or polyol C) is selected from ethylene glycol, triethylene glycol, butane-1,4-diol, propane-1,2-diol, pentane-1,5-diol, hexane-1,6-diol, cyclohexanedimethanol, decanediol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, trimethylolpropane, 2,2-dimethylpropane-1,3-diol (neopentyl glycol), neopentyl glycol hydroxypivalate or cis/trans-cyclohexane-1,4-diol, alone or in admixture.

9. The alkoxysilane-functionalized and allophanate-functionalized coating material according to claim 1, wherein the diol and/or polyol C) is selected from pentane-1,5-diol, hexane-1,6-diol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, 2,2-dimethylpropane-1,3-diol (neopentyl glycol) or cis/trans-cyclohexane-1,4-diol, alone or in admixture.

10. The alkoxysilane-functionalized and allophanate-functionalized coating material according to claim 1, wherein the diol and/or polyol C) is selected from hydroxyl-containing polyesters, polyethers, polyacrylates, polycarbonates or polyurethanes having an OH number of from 20 to 500 mg KOH/g and an average molar mass of from 250 to 6000 g/mol, alone or in admixture.

11. The alkoxysilane-functionalized and allophanate-functionalized coating material according to claim 1, wherein the diol and/or polyol C) is selected from hydroxyl-containing polyesters or polyacrylates having an OH number of from 50 to 250 mg KOH/g and an average molecular weight of from 500 to 6000 g/mol, alone or in admixture.

12. The alkoxysilane-functionalized and allophanate-functionalized coating material according to claim 1, wherein the at least one catalyst K) is selected from the group consisting of metal carboxylates, tert-amines, amidine, guanidine, quaternary ammonium salts, tetraalkylammonium salts, quaternary phosphonium salts, metal acetylacetonates, quaternary ammonium acetylacetonates, quaternary phosphonium acetylacetonates, carboxylic acids, aluminium alkoxides, zirconium alkoxides, titanium alkoxides and/or boron alkoxides and/or esters thereof, and sulphonic acids, alone or in admixture.

13. The alkoxysilane-functionalized and allophanate-functionalized coating material according to claim 1, wherein the at least one catalyst K) is zinc acetylacetonate and/or zinc ethylhexanoate.

14. The alkoxysilane-functionalized and allophanate-functionalized coating material according to claim 1, wherein the binder component b) is selected from hydroxyl-containing polyesters, polyethers, polyacrylates, polycarbonates or polyurethanes having an OH number of from 20 to 500 mg KOH/g and an average molar mass of from 250 to 6000 g/mol, alone or in admixture.

15. The alkoxysilane-functionalized and allophanate-functionalized coating material according to claim 1, wherein the binder component b) is selected from hydroxyl-containing polyesters or polyacrylates having an OH number of from 50 to 250 mg KOH/g and an average molecular weight of from 500 to 6000 g/mol, alone or in admixture.

16. The alkoxysilane-functionalized and allophanate-functionalized coating material according to claim 1, wherein the binder component b) is at least one adduct of an isocyanatotrialkoxysilane and a mono- or polyhydric alcohol.

17. The alkoxysilane-functionalized and allophanate-functionalized coating material according to claim 1, wherein at least one derivative of hydroxyl-containing polyethers, polyesters, polycarbonatediols or polyacrylates with isocyanatopropyltrialkoxysilane, alone or in mixtures, is present as the binder component b).

18. The alkoxysilane-functionalized and allophanate-functionalized coating material according to claim 1, wherein the binder component b) is aminopropyltriethoxysilane, aminomethyltrimethoxysilane or aminomethyltriethoxysilane, alone or in admixture.

19. The alkoxysilane-functionalized and allophanate-functionalized coating material according to claim 1, wherein c) is a polyisocyanate selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), or xylylene diisocyanate (MXDI), individually or in admixture.

20. The alkoxysilane-functionalized and allophanate-functionalized coating material according to claim 1, wherein component c) is an isocyanurate.

21. The alkoxysilane-functionalized and allophanate-functionalized coating material according to claim 1, wherein c) is an isocyanurate selected from the group consisting of IPDI and HDI.

22. The alkoxysilane-functionalized and allophanate-functionalized coating material according to claim 1, wherein the at least one catalyst is selected from the group consisting of metal carboxylates, tert-amines, amidine, guanidine, quaternary ammonium salts, tetraalkylammonium salts, quaternary phosphonium salts, metal acetylacetonates, quaternary ammonium acetylacetonates, quaternary phosphonium acetylacetonates, carboxylic acids, aluminium alkoxides, zirconium alkoxides, titanium alkoxides and/or boron alkoxides and/or esters thereof, and sulphonic acids, alone or in admixture.

23. The alkoxysilane-functionalized and allophanate-functionalized coating material according to claim 1, wherein the at least one catalyst is selected from tetraethylammonium benzoate, tetrabutylammonium hydroxide, tetraethylammonium acetylacetonate, tetrabutylammonium acetylacetonate, dibutyltin dilaurate, zinc acetylacetonate, or zinc ethylhexanoate.

24. The alkoxysilane-functionalized and allophanate-functionalized coating material according to claim 1, wherein solvents, stabilizers, light stabilizers, additional crosslinkers, fillers, pigments, flow control agents or rheological assistants, alone or in admixture, are employed as auxiliaries and/or additives.

25. Compositions including paint compositions, adhesive compositions, sealant compositions and metal-coating compositions wherein the compositions comprise the alkoxysilane-functionalized, allophanate-containing coating material according to claim 1.

* * * * *